(12) United States Patent
Kiester

(10) Patent No.: US 8,425,564 B2
(45) Date of Patent: Apr. 23, 2013

(54) SPINE RECONSTRUCTION ROD EXTENDER

(76) Inventor: P. Douglas Kiester, Irvine, CA (US)

( * ) Notice: Subject to any disclaimer, the term of this patent is extended or adjusted under 35 U.S.C. 154(b) by 1148 days.

(21) Appl. No.: 11/968,749

(22) Filed: Jan. 3, 2008

(65) Prior Publication Data

US 2009/0177232 A1    Jul. 9, 2009

(51) Int. Cl.
*A61B 17/70* (2006.01)
(52) U.S. Cl.
USPC .................. 606/260; 606/259; 606/261
(58) Field of Classification Search .......... 606/258–261, 606/71
See application file for complete search history.

(56) References Cited

U.S. PATENT DOCUMENTS

| | | | |
|---|---|---|---|
| 6,379,354 B1 * | 4/2002 | Rogozinski | 606/260 |
| 2004/0049189 A1 * | 3/2004 | Le Couedic et al. | 606/61 |
| 2005/0038432 A1 * | 2/2005 | Shaolian et al. | 606/61 |
| 2006/0212033 A1 * | 9/2006 | Rothman et al. | 606/61 |
| 2007/0270814 A1 * | 11/2007 | Lim et al. | 606/61 |
| 2007/0270820 A1 * | 11/2007 | Dickinson et al. | 606/61 |

* cited by examiner

*Primary Examiner* — Eduardo C Robert
*Assistant Examiner* — Julianna N Harvey
(74) *Attorney, Agent, or Firm* — CIONCA Law Group P.C.; Marin Cionca

(57) ABSTRACT

A spine reconstruction rod extender may be used to extend an existing spine reconstruction rod without skipping a pedicle screw in the new construct, exposing the entire old construct, or adding a significant amount of size to the junction between the old and new construct. The resulting extended rod is a strong, durable inline spine reconstruction rod extender.

13 Claims, 8 Drawing Sheets

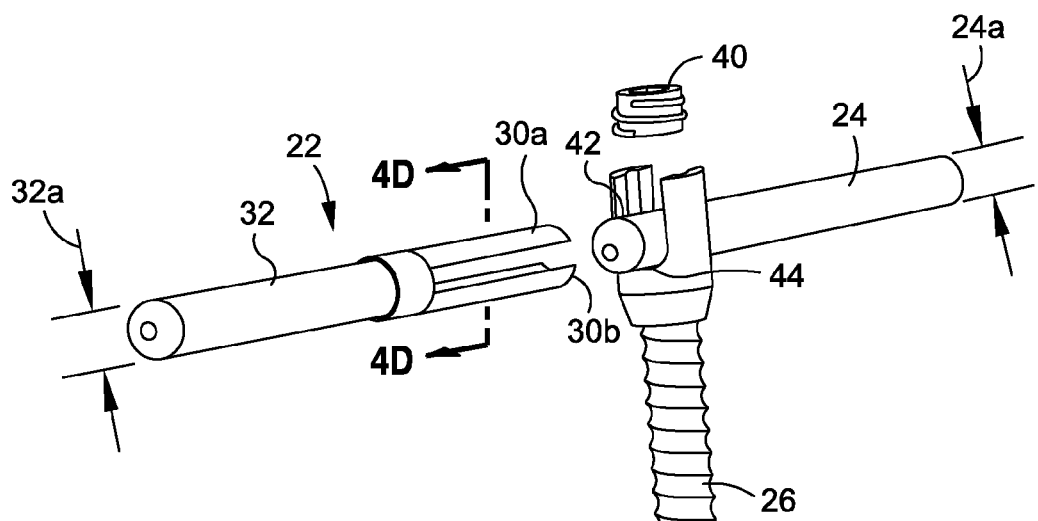
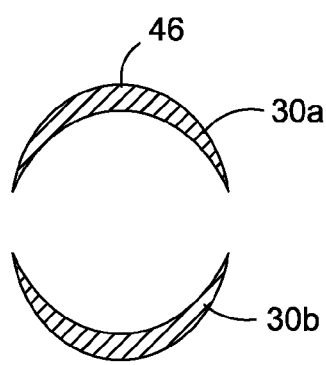
FIG. 4D
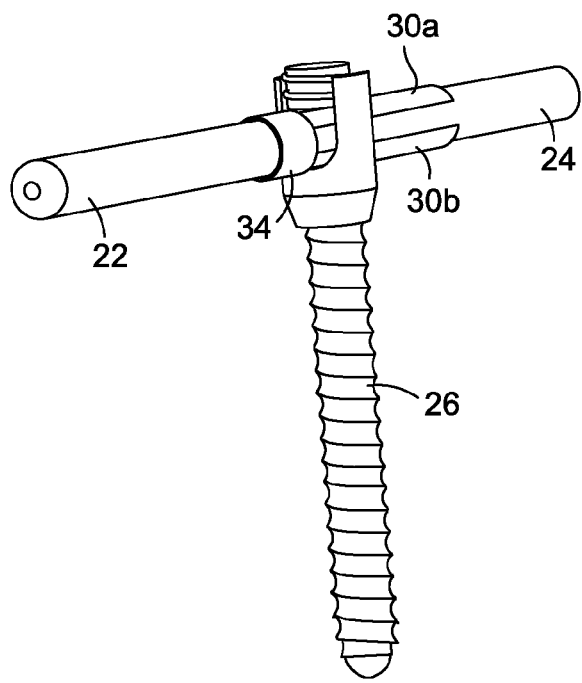
FIG. 4C
FIG. 4E

SPINE RECONSTRUCTION ROD EXTENDER

BACKGROUND OF THE INVENTION

The present invention generally relates to apparatus and methods for extending a spine reconstruction rod and, more specifically, to an apparatus and method for providing a strong, durable inline extension of a spine reconstruction rod.

Referring to FIG. 1, modern reconstructive spine surgery often involves a construct 10 of pedicle screws 12 (only one is shown in the Figure) and a rod 14. FIG. 1 shows a last pedicle screw 12 at an end 16 of the rod 14. One of the major problems with these constructs 10 is that patients will often develop adjacent level disease. It is currently unknown if adjacent level disease is caused by the surgical construct or the result of natural progression of the original condition. It may be a combination of the two causes.

Either way, the adjacent level disease will often make it necessary for the patient to come back later and extend the original construct (e.g., construct 10) up or down the spine. A problem with this extension procedure is how to lengthen the rod to incorporate the new spine levels in the construct. Current methods consist of a "domino" type linkage between the old and new rods.

There are two styles of "domino" linkages. One style is side by side; the other is inline. Both styles are essentially solid blocks of metal. In the side by side, the domino clamps the new rod along the side of the old rod. For the inline configuration, one end of the old rod is slid into the domino while the new rod is slid into the other end of the domino.

A problem with the inline design is that there is not enough space to put the rod of the original construct and the rod of the new construct end to end without having an extended length of spine reconstruction rod (including the length of the domino) that is not attached to the spine with a pedicle screw. In other words, the location where a pedicle screw of the new construct would typically be attached to the spine has to be changed to a location further down (relative to the joint between the new rod and the old rod) the spine due to the domino occupying the space where the first pedicle screw of the new construct would otherwise be located.

Another problem with the inline design is that often there is not enough of a length 16a of rod left on the original construct past the last pedicle screw 26 at the end 16 of rod 14 to insert into the domino.

A problem with the side by side domino design is one of space. The new rod, being placed along side of the original rod, is no longer inline with the original rod. Typically, a rod extension should be inline with the original rod. Therefore, significant bending of the new rod is necessary to bring the new rod back inline with the original rod. This offset and bending makes the final construct weaker than if a single, longer rod were installed according to prior art methods. Such an installation of a single, longer rod, however, as discussed below, requires exposing the entire original rod for its removal. Furthermore, the additional bulk of the side by side construct is also a problem (especially in young, thin children with scoliosis).

Another conventional way to address adjacent level disease is to completely expose the original construct (often involving a very large incision when only a single level needs to be added), remove the old rod, and replace it with a longer rod to immobilize both the original and the new spine reconstruction regions.

As can be seen, there is a need for an apparatus and method for extending a reconstruction rod which does not involve skipping a pedicle screw in the new construct, exposing the entire old construct, or adding a significant amount of size to the junction between the old and new construct.

SUMMARY OF THE INVENTION

In one aspect of the present invention, a rod extender for extending an original rod comprises a rod extension base; and at least one arm attached to the rod extension base, wherein the at least one arm extends over an end of the original rod.

In another aspect of the present invention, a spine reconstruction rod extender for extending an original rod comprises a rod extension base; and a first arm and a second arm attached to and extending from the rod extension base, wherein the first arm fits into a rod receiving portion of a last pedicle screw of the original rod; and the second arm fits over the original rod to receive force from a set screw of the last pedicle screw.

In a further aspect of the present invention, a spine reconstruction rod extender for extending an original rod comprises a rod extension base; and a first arm having a minimum diameter smaller than a diameter of the original rod, the first arm fitting over the original rod to provide an inline extension of the original rod.

In yet a further aspect of the present invention, a method for extending a previously implanted spine reconstruction rod comprises exposing only an end of the previously implanted spine reconstruction rod, including a last pedicle screw thereof; positioning a rod extension in-line with the previously implanted spine reconstruction rod; and securing the rod extension to the previously implanted spine reconstruction rod.

In still another aspect of the present invention a method for extending a previously implanted spine reconstruction rod comprises inserting a rod extension device onto the previously implanted reconstruction rod; using an existing pedicle screw associated with the previously implanted spine reconstruction rod to secure the rod extension in-line to the previously implanted spine reconstruction rod; and omitting a connecting component not already associated with the previously implanted spine reconstruction rod to secure the rod extension to the previously implanted spine reconstruction rod.

These and other features, aspects and advantages of the present invention will become better understood with reference to the following drawings, description and claims.

BRIEF DESCRIPTION OF THE DRAWINGS

FIGS. 4A through 4E are perspective views showing a method of attaching the rod of FIG. 2, according to the present invention;

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides an apparatus and method for extending a reconstruction rod. Embodiments of the rod extender of the present invention, unlike conventional rod extenders discussed above, may not involve skipping a pedicle screw in the new construct, exposing the entire old construct, or adding the bulk of a domino to the junction between the old and new construct.

The present invention may result in an extension of an original rod into a new construct. The present invention requires exposing only the last pedicle screw of the old construct in order to extend the original rod. Moreover, the present invention may be useful when the new construct involves a different diameter rod as compared to the old construct. This occurs, for example, when a thoracic fusion needs to be extended into the neck.

As used herein, the term "construct" refers to a rod and screw assembly, for example, a spine reconstruction rod and pedicle screw assembly. An "old construct" or "original construct" refers to a rod and pedicle screw assembly previously implanted in a patient. A "new construct" refers to a rod and pedicle screw assembly to be implanted in a patient, for example, a "new construct" could refer to an original new implant or to an extension for an old construct.

As used herein, the term "last", when referring to a "last pedicle screw" in an original construct, refers to the pedicle screw in the original construct which is located immediately adjacent to (without a pedicle screw therebetween) one end of the original rod. Typically, the "last pedicle screw" of the original construct refers to the pedicle screw at an end of the original rod from which an extension of that original rod is desired.

As used herein, the term "first", when referring to a "first pedicle screw" in a new construct, refers to the pedicle screw in the new construct which is located immediately adjacent to (without another pedicle screw therebetween) one end of the new construct, this end being the end of the new construct adjacent to the end of the original construct being extended.

Figure 2:
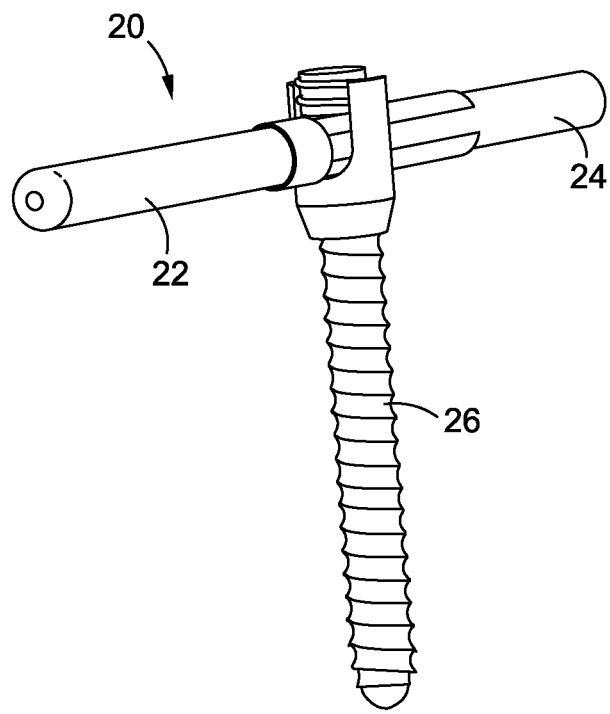
FIG. 2 is a perspective view of a rod extension according to the present invention.

Referring to FIG. 2, there is shown a perspective view of an exemplary construct 20 according to the present invention. The construct 20 may include a rod extension 22 which may fit onto an original rod 24 near the location of the last pedicle screw 26 of the original rod 24. The assembly of the construct will be discussed with reference to FIGS. 4A through 4C.

Figure 3:
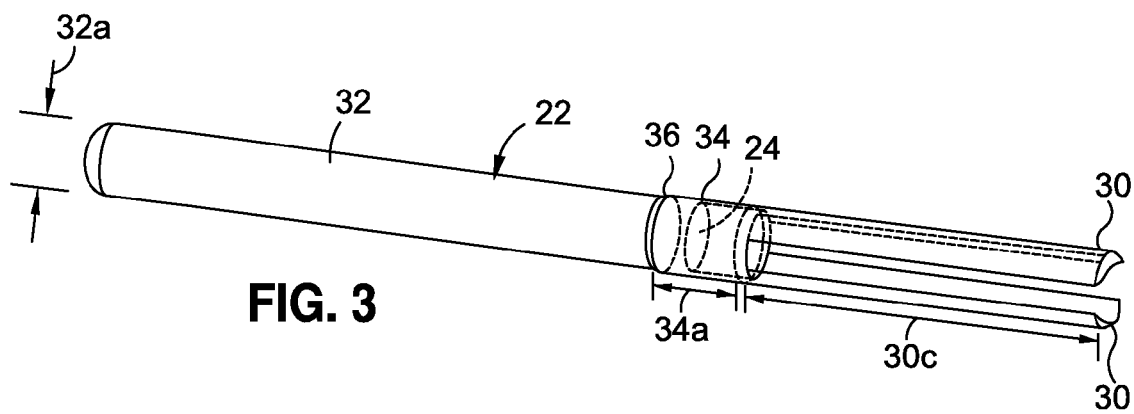
FIG. 3 is a perspective view of the rod extension of FIG. 2 being joined to an existing rod, according to the present invention.

Referring to FIG. 3, there is shown a perspective view of the rod extension 22 of FIG. 2 being inserted over the original rod 24 (shown by dashed lines), according to the present invention. The rod extension 22 may include arms 30 projecting from a rod extension body 32. The rod extension 22 may include a hollow sleeve portion 34 at an end 36 of the rod extension body 32. The hollow sleeve portion 34 may receive the original rod 24 as shown in FIG. 3. When fully in place, the original rod 24 may come close to (for example, within about 1-4 mm) or may abut against the end 36 of the rod extension body 32. With the rod extension body 32 being close to the original rod 24, the location where the first pedicle screw (not shown) attaches to the rod extension body 32 of the rod extension 22 is not blocked, as may be the case with conventional rod extensions which use dominos that extend beyond the location where the first pedicle screw would attach to conventional rod extensions.

The sleeve portion 34 may be any suitable length 34a for providing support for the original rod 24 therewithin, and typically will be from about 6 to about 20 mm in length. The arms 30 also may be of any suitable length 30c for providing attachment of the rod extension 22 to original rod 24, and typically will be from about 1 to about 1.5 cm in length.

The rod extension body 32 may have a diameter 32a similar to those rods typically used in the past for spine reconstruction. For example, the present invention may include rod extension bodies 32 having diameters of 6.35 mm, 5.5 mm, 3.5 mm and the like. Furthermore, the rod extension 22 of the present invention may be used with any type of original rod 24, including both rigid rods and flexible rods.

Figure 4A:
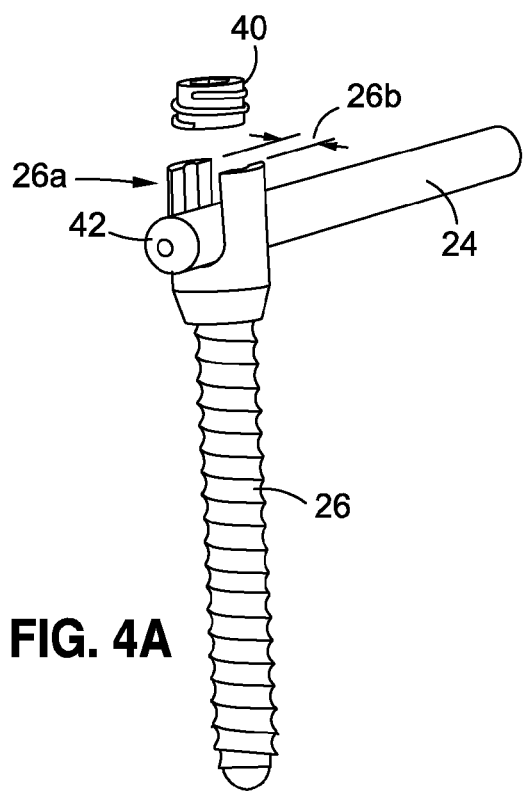

Referring to FIGS. 4A through 4E, there are shown, graphically, steps for extending the original rod 24 with a rod extension 22. In FIG. 4A, a set screw 40 may be loosened or removed from the last pedicle screw 26 at an end 42 of the original rod 24. The rod extension 22 of the present invention may require the surgical exposure of only the end 42 and the last pedicle screw 26 of the original rod 24.

Figure 4B:
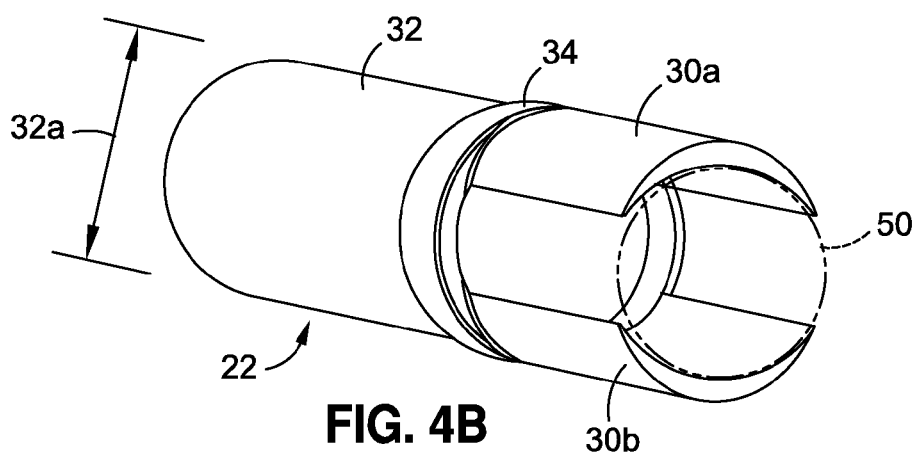

In FIG. 4B, a dotted line 50 shows an outer circumference of the original rod 24 when inserted in between the arms 30a, 30b. The diameter (not specifically shown) of the sleeve portion 34 may be larger than the original rod 24 (not shown), as the sleeve portion 34 may not need to fit into the rod receiving portion 26a of the pedicle screw 26. The rod extension body 32 may have a diameter 32a depending upon the particular application. For example, the rod extension body 32 may have a diameter that is the same as the original rod 24, that is larger than the original rod 24, or that is smaller than the original rod 24. Selection of the appropriate sized rod extension body 32 may be recognized as within the ability of one skilled in the spine reconstruction arts.

In FIG. 4C, the arms 30a, 30b of the rod extension 22 may slide over the end 42 of the original rod 24. One arm 30a may be aligned to contact the set screw 40 when the set screw 40 is replaced onto the pedicle screw 26. The other arm 30b may be aligned to meet a bottom portion 44 of the pedicle screw 26 as shown in FIG. 4C.

Typically, a rod receiving portion 26a of the pedicle screw 26 (see FIG. 4A) has width 26b sized to match the diameter 24a of the original rod 24. For this reason, the arms 30a, 30b of the rod extension 22 may fit into the rod receiving portion 26a when aligned as described above (i.e., with the arms being at the bottom portion 44 of the pedicle screw 26 and at the top of the rod receiving portion 26a). This configuration may allow the arms 30a, 30b to fit into the rod receiving portion 26a of the pedicle screw 26 without requiring changing the pedicle screw 26 or resizing the rod receiving portion 26a.

FIGS. 4A through 4C show the arms having curvature similar to that of the original rod 24. Such curvature is useful, especially for the lower arm 30b, so that the lower arm 30b may fit into the bottom portion 44 of the pedicle screw 26 in a manner similar to that of the original rod 24. The upper arm 30a, however, may be shaped similar to that of the original rod 24 or, alternatively, may have a flattened top portion 46, as shown in FIG. 4D, which is a cross-sectional view of the rod extension 22 along line 4D-4D of FIG. 4C. The flattened top portion 46 may be useful to provide a flat surface to contact a bottom of the set screw 40 when the set screw 40 is reassembled into the pedicle screw 26.

Figure 1:
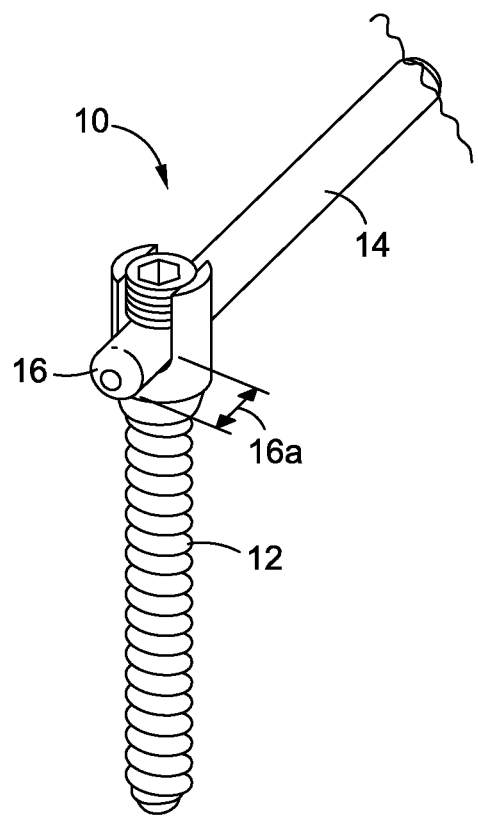
FIG. 1 is a perspective view of a pedicle screw and rod according to the prior art.

In FIG. 4E, the reassembly of the set screw 40 into the pedicle screw 26 with the rod extension 22 in place is shown. As discussed above, the original rod 24 may slide into the arms 30a, 30b of the rod extension 22 and fit into the sleeve portion 34 of the rod extension 22 as shown in FIG. 4E. Once installed, the rod extension 22 may be secured to the spine by one or more new pedicle screws in a manner similar to conventional rods (see, for example, FIG. 1).

Figure 5:
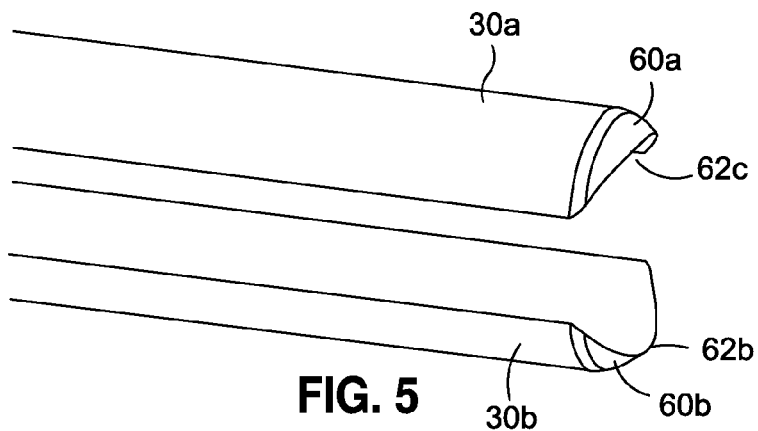
FIG. 5 is a close up view of a rod having a sharp end according to the present invention.
Figure 6:
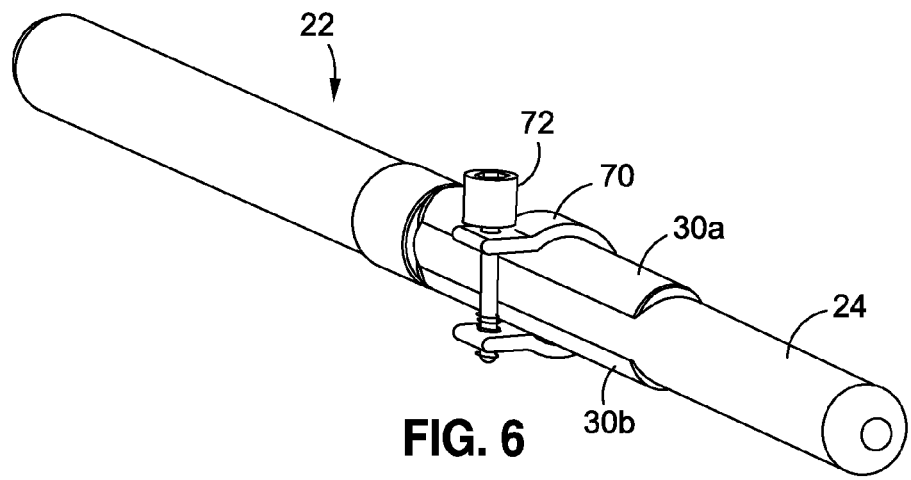
FIG. 6 is a perspective view of a clamp used to affix an existing rod to the rod of the present invention.

Referring now to FIG. 5, there is shown an exemplary configuration of the ends 60a, 60b of the arms 30a, 30b of the rod extension 22. In this embodiment, the arms 30a, 30b may be optionally "sharp", as shown in FIG. 6, so as to assist in sliding the arms 30a, 30b over the original rod 24. "Sharp" ends 60a, 60b, as the term is used here, may result in leading edges 62a, 62b of the ends 60a, 60b of the arms 30a, 30b to have a thickness (not shown) smaller than the thickness of the remaining portions of the arms 30a, 30b.

Referring to FIG. 6, there is shown the rod extension 22 of the present invention attached to the original rod 24 in an alternate configuration as described below. A clamp 70 may be used to affix the rod extension 22 to the original rod 24 according to the present invention. When the end 42 (not shown) of the original rod 24 (see FIG. 4C) extends past the last pedicle screw 26 to allow the rod extension 22 to fit over this extending end 42 without contacting the last pedicle screw 26 (not shown, located along the original rod 24, distal to the interface of the rod extension 22 and the original rod 24), the clamp 70 may be used in place of the pedicle screw 26/set screw 40 combination to attach the rod extension 22 to the original rod 24. The clamp 70 may be any biocompatible clamp suitable for applying pressure around a rod. The clamp 70 may include a screw 72 or other means for tightening the clamp 70 on the arms 30a, 30b of the rod extension 22, thereby frictionally attaching the rod extension 22 to the original rod 24.

Figure 7:
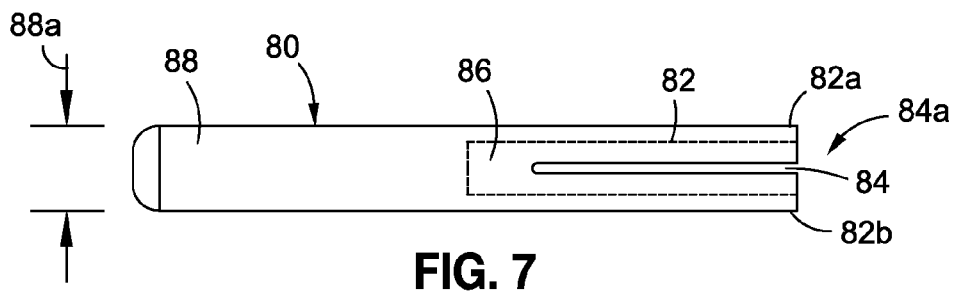
FIG. 7 is a partial cut away plan view of a rod used to change rod diameter of a construct, according to the present invention.
Figure 8:
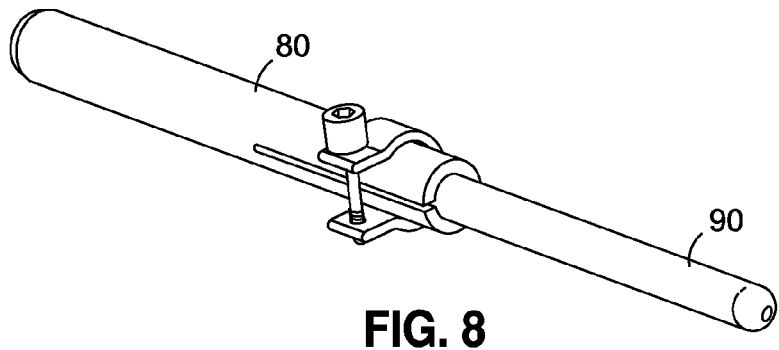
FIG. 8 is a perspective view showing a change in rod diameter with a clamp, according to the present invention.
Figure 9:
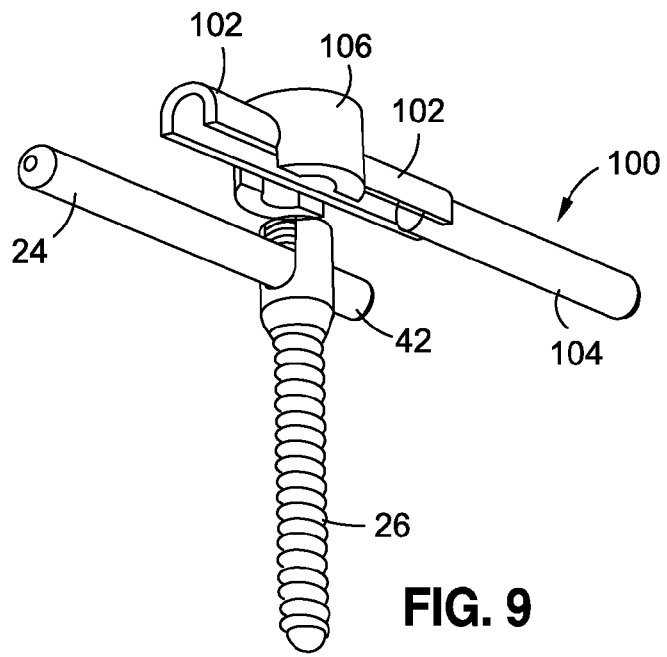
FIG. 9 is a perspective view showing a rod extension device according to the present invention.

Referring to FIG. 7, there is shown an alternate embodiment of the present invention wherein a size adjusting rod 80 may extend an original rod 90 (see FIG. 8) into a rod extension body 88 having a larger diameter 88a than that of the original rod 90 according to the present invention. Dotted lines 82 may show where a new rod 90 (see FIG. 8) may be inserted. The size adjusting rod 80 may include arms 82a, 82b separated by a slot 84, and a sleeve portion 86, similar to the rod extension 22 described above. In one embodiment of the present invention, the size adjusting rod 80 may be an original implant in a patient where a future implant may be needed. For example, the size adjusting rod 80 may be implanted in a thoracic spine reconstruction. The end 84a and the slots 84 (only one shown) of the size adjusting rod 80 may be filled with a spacer (not shown). The spacer may be any biocompatible spacer to prevent tissue growth inside the size adjusting rod 80. If the patient later needs cervical spine fixation, the spacer can be removed and the new rod 90 may be inserted and clamped as shown in FIG. 9. This size adjusting configuration, using size adjusting rod 80, may also be used acutely, for example, when doing thoracic and cervical spine fixation at the same time.

Figure 10:
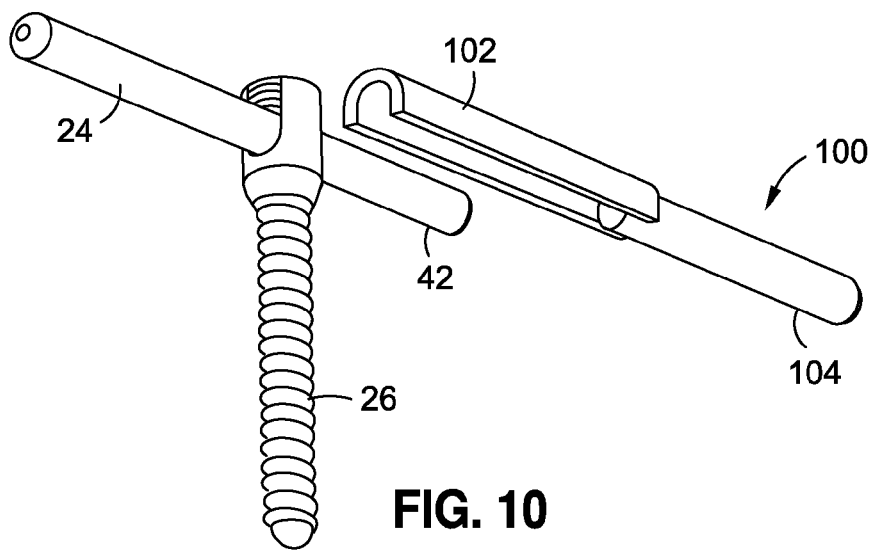
FIG. 10 is a perspective view showing a rod extension device without a pedicle screw cover according to the present invention.

Referring now to FIG. 9, there is shown a perspective view of a rod extension 100 according to another exemplary embodiment of the present invention. The rod extension 100 is similar to the rod extension 22 described above in that the rod extension 100 has an arm 102 that fits over the original rod 24. Similar to the rod extension 22, rod extension 100 may provide inline extension of the original rod 24. Alternatively, the rod extension 100 may provide an offset (not shown) between the rod extension body 104 and the original rod 24. The rod extension 100 may include a pedicle screw fitting portion 106 which may fit over the last pedicle screw 26 of the original rod 24. However, the pedicle screw fitting portion 106 may be present along any portion of the arm 102. As shown in FIG. 9, the pedicle screw fitting portion 106 may be centrally located along the arm 102. Where there may be sufficient amount of original rod 24 extending beyond the last pedicle screw 26 (the end portion 42 of the original rod 24) so that the arm 102 does not contact the last pedicle screw 26 of the original rod 24, the pedicle screw fitting portion 106 may not be necessary, as the entire arm 102 may fit onto the end portion 42, as shown in FIG. 10. Unlike conventional inline domino extensions, which may require a significant length of the end 42 extending beyond the last pedicle screw 26 for which to attach the domino, the present invention may be used to extend original rods 24 which do not have long ends 42 extending beyond the last pedicle screw 26.

Figure 11:
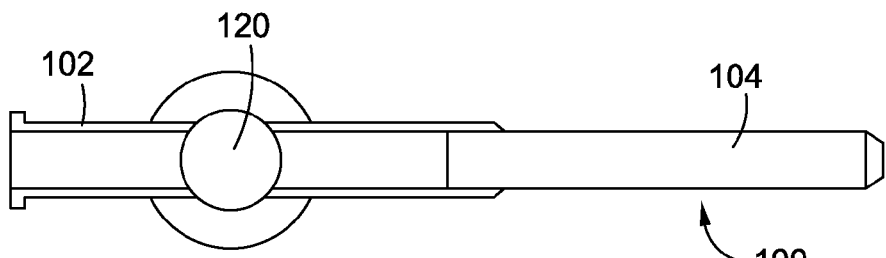
FIG. 11 is a plan view of the rod extension device of FIG. 9 installed on an original rod.

Referring to FIG. 11, there is shown a plan view of the rod extension 100 according to the present invention. The pedicle screw fitting portion 106 may include an opening 120 allowing access to the set screw 40 (not shown) of the pedicle screw 26. Typically, fitting the arm 102 of the rod extension 100 of the present invention over the original rod 25 may not require loosening or adjustment of the set screw 40. However, should adjustment be necessary, the opening 120 may provide access thereto.

Figure 12:
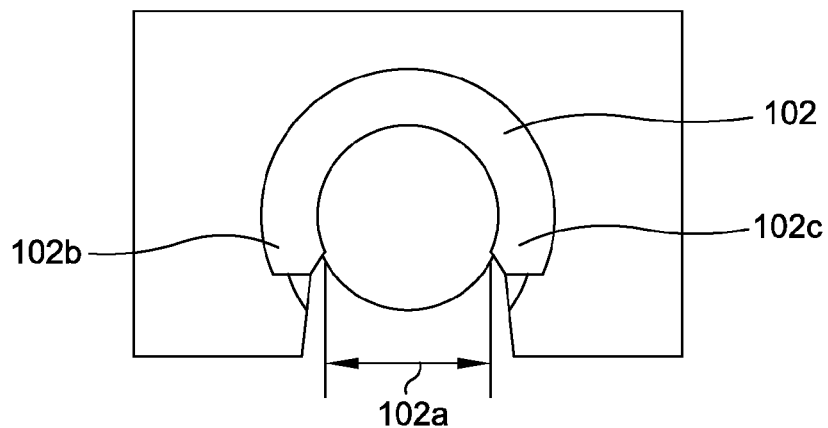
FIG. 12 is an end view of the rod extension device of FIG. 9.

Referring to FIG. 12, there is shown an end view of the rod extension 100 according to the present invention. The arm 102 of the rod extension 100 may have a minimum diameter 102a that is smaller than the diameter 24a of the original rod 24 (see FIG. 4C). The arm 102 may form a semi-circle shape that is more than 180 degrees (more than half a circle). With this configuration, the original rod 24 may fit into the arm 102 of the rod extension 100 by applying a force to open the ends 102b, 102c of the arms to allow the original rod 24 to fit in place. Once installed, a similar, opposite force may be needed to remove the original rod 24 from the arm 102. This configuration may help keep the two components of the new construct (the rod extension 100 and the original rod 24) joined together.

Figure 13A:
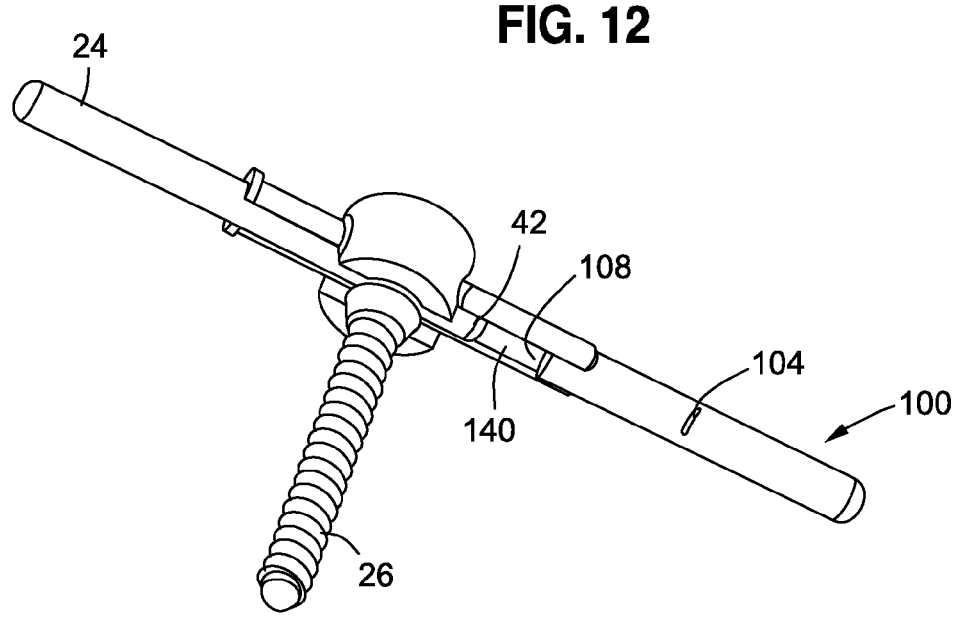
FIG. 13A is a bottom perspective view of the rod extension device of FIG. 9, showing the last pedicle screw of the original rod.
Figure 13B:
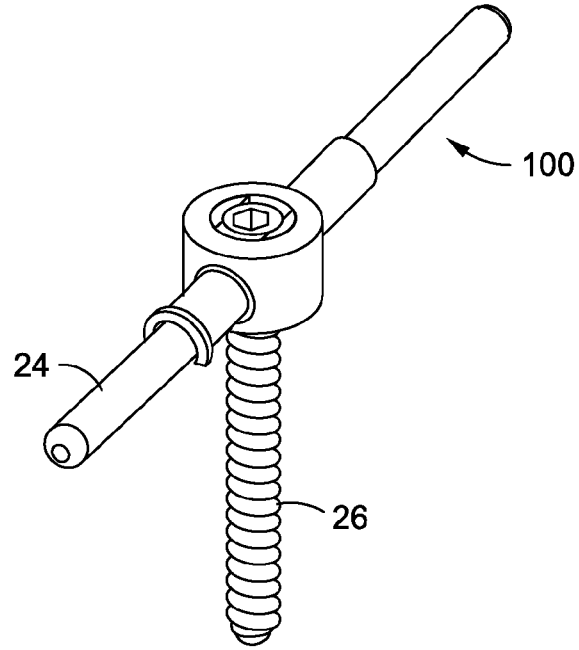
FIG. 13B is a top perspective view of the rod extension device of FIG. 9, showing the last pedicle screw of the original rod.

Referring now to FIGS. 13A and 13B, there are shown perspective views of the rod extension 100 attached to the original rod 24. Referring specifically to FIG. 13A, a space 140 may be present between the end 42 of the original rod 24 and the end 108 of the rod extension body 104. Depending upon the amount of the original rod 24 that extends beyond the last pedicle screw 26, this space 140 may be from zero to about 8 mm or longer. Typically, this space 140 may be between about 1 mm to about 6 mm. Minimizing the space 140 may minimize the leverage placed on the linkage between the original rod and the rod extension.

Figure 14A:
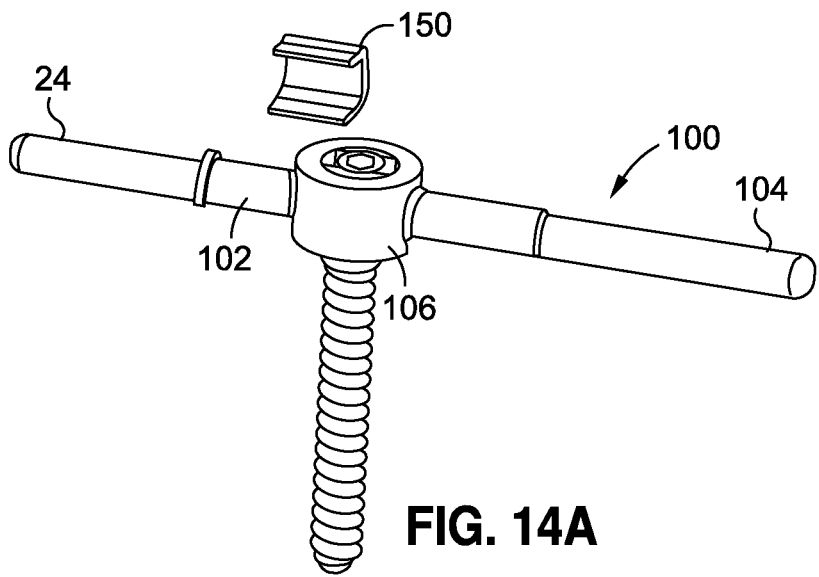
FIGS. 14A through 14C show steps for applying a clamp to the rod extension device of FIG. 12.
Figure 14B:
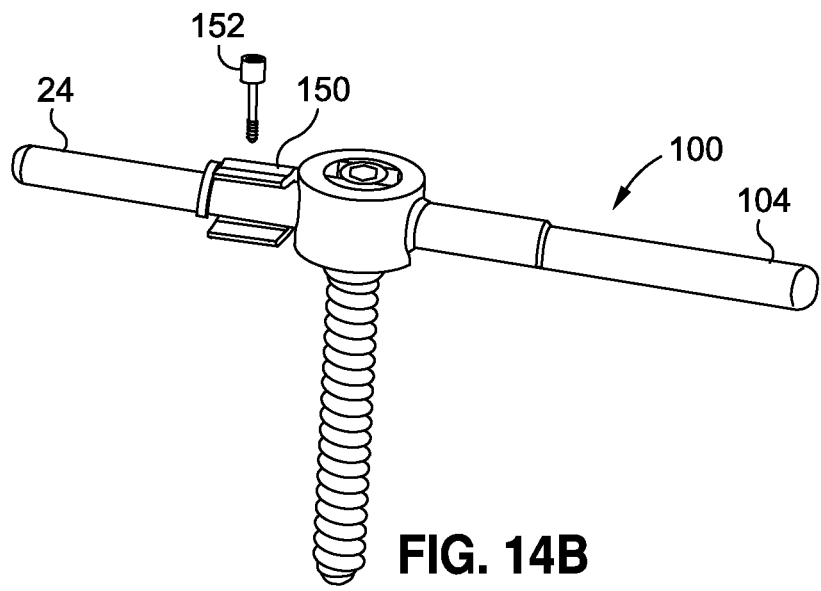
Figure 14C:
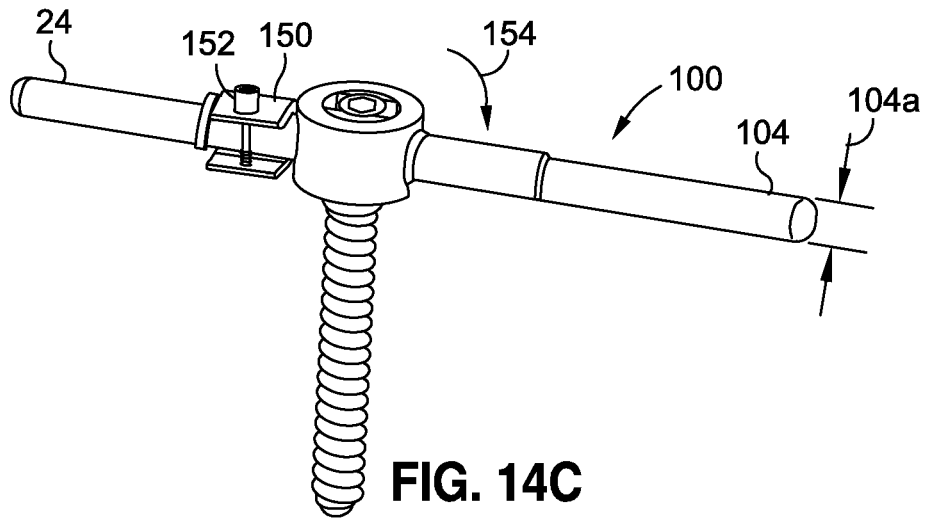

Referring to FIGS. 14A through 14C there is shown, graphically, a method for extending the original rod 24 with the rod extension 100. In FIG. 14A, the rod extension 100 may be placed over the original rod 24 with the pedicle screw fitting portion 106 fitting over the pedicle screw 26. A clamp 150 may be opened and aligned next to the arm 102 of the rod extension 100. In FIG. 14B, the clamp 150 is placed around the arm 102 and original rod 24 and a clamp screw 152 may be aligned to be inserted into the clamp. In FIG. 14C, the clamp screw 152 may be inserted into the clamp 150 and tightened, thereby providing a frictional fit between the arm 102 and the original rod 24. While FIGS. 14A through 14C show the clamp 150 on the arm 102 distal to the pedicle screw fitting portion 106, the clamp 150 may be placed, as an alternate to, or in addition to the configuration shown in the figures, on the arm 102 proximate to the pedicle screw fitting portion 106 (as shown by arrow 154 in FIG. 14C), where distal and proximate refer to the pedicle screw fitting portion 106 relative to the rod extension body 104.

Similar to the rod extension 22 described above, the diameter of the rod extension body 104 (indicated as 104a in FIG. 14C) may be any diameter suitable for the intended purpose, including diameters that are the same, smaller or larger than that of the original rod 24.

Figure 15:
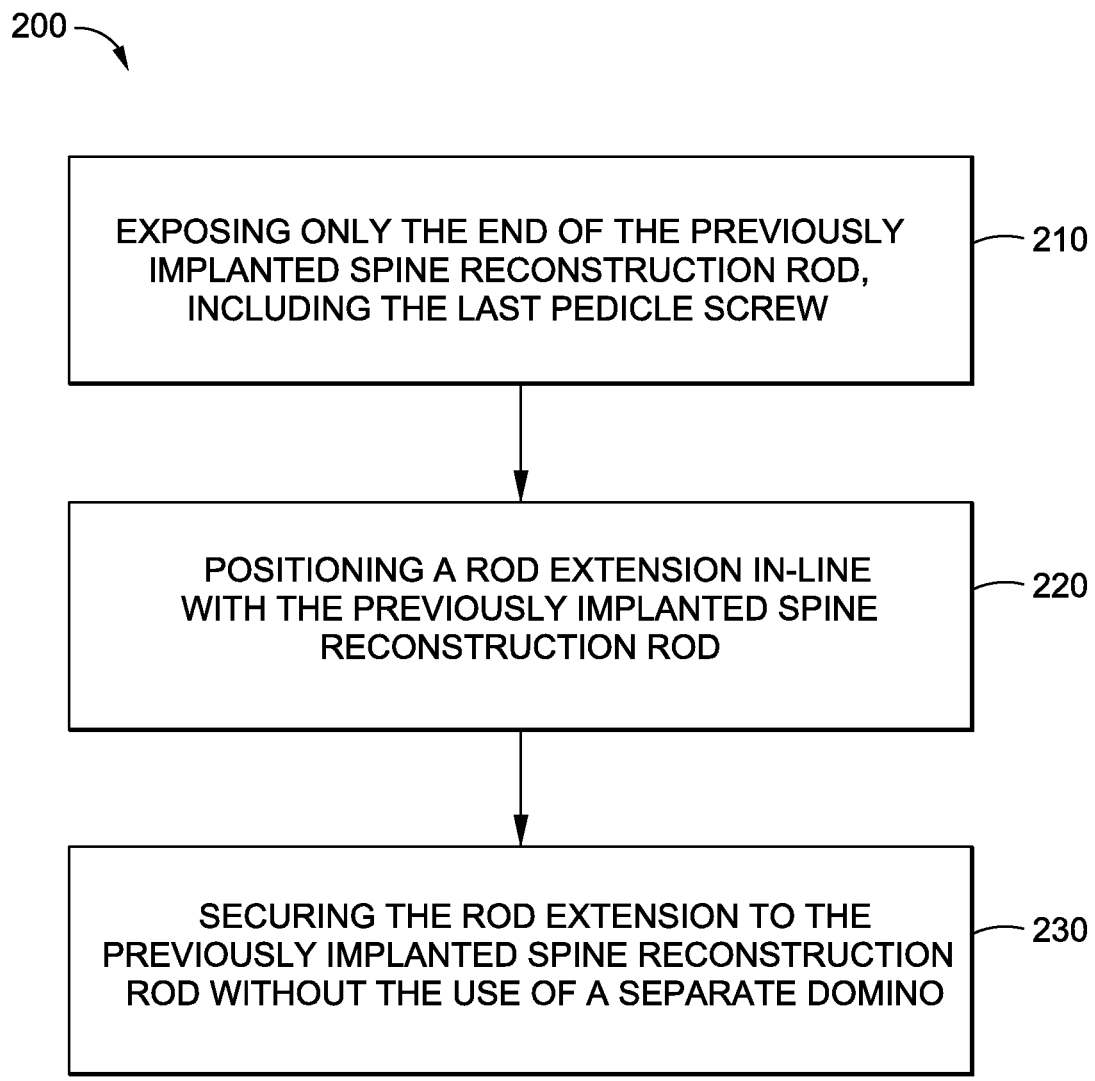
FIG. 15 is a flow chart describing a method of the present invention.

Referring to FIG. 15, there is shown a method 200 for extending a previously implanted spine reconstruction rod (e.g., original rod 24) with a rod extension (e.g., rod extension 22). The method 200 may include a step 210 of exposing only the end (e.g., end 42) of the previously implanted spine reconstruction rod, including the last pedicle screw (e.g., last pedicle screw 26). Unlike conventional methods, which may require exposure of the entire length of the previously implanted rod, the present invention may only require exposure of the end of the previously implanted rod adjacent to where the new construct (rod extension) is to be added.

Once the end of the previously implanted rod is exposed, the method 200 may include a step 220 of positioning the rod extension in-line with the previously implanted spine reconstruction rod. According to one aspect of the present invention, the rod extension may be positioned with its end abutting the end of the previously implanted spine reconstruction rod. Unlike conventional methods, which may place the new rod along side of the original rod and then bend the new rod to be inline with the original rod, the present invention does not require such a bending which may weaken the spine reconstruction rod.

Finally, once the rod extension is positioned, the method 200 may include a step 230 of securing the rod extension to the previously implanted spine reconstruction rod without the use of a separate domino. The securing step 230 may performed by, for example, a) clamping one arm from the rod extension to the original rod; b) clamping two arms from the rod extension to the original rod; or c) securing at least one arm from the rod extension to a set screw of the last pedicle screw of the original rod.

Both the rod extension 22 and the rod extension 100 may have arms (30, 30a, 30b or 102, respectively) that are relatively thin. For example, the arms may be from about 0.1 to about 0.4 mm thick, typically about 0.2 mm thick. While not agreeing to any one theory, there are several reasons why the arms joining the rods may be made thin. For example, the ends of the rods (ends 42 and 108, for example) may be brought close together, as discussed above. This closeness may minimize the leverage placed on the linkage between the original rod and the rod extension. Additionally, even though the arms themselves are thin, when the rod extensions are connected to the original arms, the thickness at the junction is slightly larger than the rods themselves, as discussed above, thus strengthening the region where the rods (the original and the extension) are joined. Finally, with respect to rod extension 22, the original rod may slide into a sleeve of the rod extension. This configuration may give circumferential linkage further strengthening to the junction between the two rods.

It should be understood, of course, that the foregoing relates to exemplary embodiments of the invention and that modifications may be made without departing from the spirit and scope of the invention as set forth in the following claims.

I claim:

1. A rod extender for extending an original rod, the rod extender comprising: a rod extension base; and at least one arm attached to the rod extension base, wherein the at least one arm is configured to extend over an end of the original rod, wherein the original rod is a solid rod having same diameter throughout, to fit into the rod receiving portion of the last pedicle screw of the original rod, and to create an in-line joint which is substantially longer than wide or tall, and taller than wide, wherein the width of the created in-line joint, the diameter of the original rod and the width of said receiving portion are equal, and wherein the in-line joint is positioned at least partially within said receiving portion so that said in-line joint is capable of being secured with the set screw of the last pedicle screw of the original rod.

2. The rod extender according to claim 1, further comprising a first arm and a second arm extending over the end of the original rod.

3. The rod extender according to claim 2, further comprising a hollow sleeve portion located between the rod extension base and the first arm and the second arm, the hollow sleeve portion receiving the end of the original rod.

4. The rod extender according to claim 2, wherein: the first arm fits into a rod receiving portion of a last pedicle screw of the original rod; and the second arm fits over the original rod to receive force from a set screw of the last pedicle screw.

5. The rod extender according to claim 2, wherein ends of the first arm and the second arm have a sharp leading edge to assist sliding the rod extender on the original rod.

6. The rod extender according to claim 1, wherein the rod extension base has a diameter different from a diameter of the original rod.

7. The rod extender according to claim 6, wherein the original rod and the rod extender are components of an original spine reconstruction implant.

8. The rod extender according to claim 1, wherein an end of the original rod abuts against the rod extension base of the rod extender.

9. A method for extending a previously implanted spine reconstruction rod, the method comprising: exposing only an end of the previously implanted spine reconstruction rod, including a last pedicle screw thereof; positioning a rod extension in-line with the previously implanted spine reconstruction rod such that a taller than wide in-line joint is created which fits into the rod receiving portion of the last pedicle screw, and such that the in-line joint's width, the diameter of the previously implanted spine reconstruction rod and the width of said receiving portion are equal; and securing the rod extension to the previously implanted spine reconstruction rod and to the last pedicle screw by using only the set screw of the last pedicle screw, in the same manner as previously used to secure the previously implanted spine reconstruction rod to the last pedicle screw, such that no other components are added or removed.

10. The method of claim 9, further comprising abutting an end of the rod extension to the end of the previously implanted spine reconstruction rod.

11. A method for extending a previously implanted spine reconstruction rod, the method comprising: inserting a rod extension device onto the previously implanted reconstruction rod; using an existing pedicle screw associated with the previously implanted spine reconstruction rod to secure the rod extension in-line to the previously implanted spine reconstruction rod without adding any connecting component not already associated with the previously implanted spine reconstruction rod to secure the rod extension to the previously implanted spine reconstruction rod and without removing any connecting component associated with the previously implanted spine reconstruction rod.

12. The method according to claim 11, further comprising stabilizing the rod extension by abutting an end of the rod extension device against an end of the previously implanted reconstruction rod when inserting the previously implanted reconstruction rod into the rod extension device.

13. The method according to claim 11, wherein a diameter of a rod extension body of the rod extension device differs from a diameter of the previously implanted reconstruction rod.

* * * * *